(12) United States Patent
Bhattacharya et al.

(10) Patent No.: US 10,380,497 B2
(45) Date of Patent: Aug. 13, 2019

(54) METHODS AND SYSTEMS FOR ANALYZING HEALTHCARE DATA

(71) Applicant: Conduent Business Services, LLC, Florham Park, NJ (US)

(72) Inventors: Sakyajit Bhattacharya, Bangalore (IN); Vaibhav Rajan, Bangalore (IN)

(73) Assignee: Conduent Business Services, LLC, Florham Park, NJ (US)

( * ) Notice: Subject to any disclaimer, the term of this patent is extended or adjusted under 35 U.S.C. 154(b) by 530 days.

(21) Appl. No.: 14/179,752

(22) Filed: Feb. 13, 2014

(65) Prior Publication Data
US 2015/0227691 A1 Aug. 13, 2015

(51) Int. Cl.
*G06N 7/00* (2006.01)
*G06N 20/00* (2019.01)
*G16H 10/60* (2018.01)
*G16H 50/20* (2018.01)

(52) U.S. Cl.
CPC ............ *G06N 20/00* (2019.01); *G06N 7/005* (2013.01); *G16H 10/60* (2018.01); *G16H 50/20* (2018.01)

(58) Field of Classification Search
CPC ........ G06N 7/00; G06F 19/322; G16H 50/20; G16H 10/60
See application file for complete search history.

(56) References Cited

FOREIGN PATENT DOCUMENTS

WO    WO-2013012990 A1 *  1/2013  ............. G06N 7/005

* cited by examiner

*Primary Examiner* — Sheetal R Paulson
(74) *Attorney, Agent, or Firm* — Jones Robb, PLLC

(57) ABSTRACT

Disclosed are the embodiments for creating a model capable of identifying one or more clusters in a healthcare dataset. An input is received pertaining to a range of numbers. Each number in the range of numbers is representative of a number of clusters in the healthcare dataset. For a cluster, one or more first parameters of a distribution associated with the cluster are estimated. Thereafter, a threshold value is determined based on the one or more first parameters. An inverse cumulative distribution of each of one or more n-dimensional variables in the healthcare dataset is determined. The one or more first parameters are updated to generate one or more second parameters based on the estimated inverse cumulative distribution. A model is created for each number in the range of numbers based on the one or more second parameters.

28 Claims, 4 Drawing Sheets

METHODS AND SYSTEMS FOR ANALYZING HEALTHCARE DATA

TECHNICAL FIELD

The presently disclosed embodiments are related, in general, to data mining. More particularly, the presently disclosed embodiments are related to methods and systems for analyzing healthcare data.

BACKGROUND

Healthcare industry is one industry that involves maintenance of various records from birth certificate to death certificate of a person. Such records may include, but are not limited to, medical diagnostic records, medical insurance records, hospital data, etc. This record data may be utilized to generate a mathematical model that may have a capability to identify/predict information such as, but not limited to, a health condition of a patient, and health insurance frauds. In order to generate the mathematical model, one or more patterns need to be identified in the record data.

Data mining techniques enable determination of one or more patterns in the record data. Such patterns may be used to determine clusters in the record data. Clustering is a process of grouping a set of records in the record data based on predefined characteristics associated with the set of records. Some of the commonly known clustering algorithms include, but are not limited to, k-means clustering, density-based clustering, centroid-based clustering, Gaussian mixture models, etc.

A Gaussian mixture model is a clustering technique that assumes that the record data includes one or more components or clusters and data in each cluster is normally distributed (i.e., Gaussian distribution). In order to train the Gaussian mixture model, an input pertaining to a number of clusters present in the record data is received from a user. As discussed above, data in each cluster is normally distributed. Parameters, such as mean and covariance, of the distribution for each cluster can be estimated using expectation-maximization algorithm. In an embodiment, the expectation-maximization algorithm includes determination of a likelihood that a data point or a record corresponds to a cluster. The likelihood is maximized and the parameters of the distribution that lead to the maximized likelihood are selected. The selected parameters are utilized to generate the Gaussian mixture model.

As it is assumed that the data in the clusters is normally distributed, Gaussian mixture models cannot be applied to scenarios where the data is not normally distributed.

SUMMARY

According to embodiments illustrated herein there is provided a method for creating a model capable of identifying one or more clusters in a healthcare dataset. The method comprises receiving, by one or more processors, an input pertaining to a range of numbers. Each number in the range of numbers is representative of a number of clusters in the healthcare dataset. For a cluster in the number of clusters, one or more first parameters of a distribution associated with the cluster are estimated. An inverse cumulative distribution of each of one or more n-dimensional variables in the healthcare dataset is determined based on a threshold value and a cumulative distribution of each of the one or more n-dimensional variables. The one or more first parameters are updated to generate one or more second parameters based on the estimated inverse cumulative distribution, wherein the updating is performed using an expectation-maximization algorithm. Finally, the model is created for each number in the range of numbers based on the one or more second parameters associated with each cluster in the number of clusters.

According to embodiment illustrated herein there is provided a system for creating a model capable of identifying one or more clusters in a healthcare dataset. The system comprising one or more processors configured to receive an input pertaining to a range of numbers. Each number in the range of numbers is representative of a number of clusters in the healthcare dataset. Further, the one or more processors are configured to estimate one or more first parameters of a distribution associated with a cluster from the number of clusters. The one or more processors are further configured to determine a threshold value based on the one or more first parameters. An inverse cumulative distribution of each of one or more n-dimensional variables in the healthcare dataset is estimated, by the one or more processors, based on the threshold value and a cumulative distribution of each of the one or more n-dimensional variables. The one or more processors are configured to update the one or more first parameters to generate one or more second parameters based on the estimated inverse cumulative distribution, wherein the updating is performed using an expectation-maximization algorithm. The one or more processors are configured to create the model for each number in the range of numbers based on the one or more second parameters associated with each cluster in the number of clusters.

According to embodiment illustrated herein there is provided a computer program product for use with a computing device. The computer program product comprising a non-transitory computer readable medium. The non-transitory computer readable medium stores a computer program code for creating a model capable of identifying one or more clusters in a healthcare dataset. The computer program code is executable by one or more processors in the computing device to receive an input pertaining to a range of numbers. Each number in the range of numbers is representative of a number of clusters in the healthcare dataset. For a cluster in the number of clusters, the computer program code is executable to estimate one or more first parameters of a distribution associated with the cluster. Thereafter, a threshold value is determined based on the one or more first parameters. An inverse cumulative distribution of each of one or more n-dimensional variables in the healthcare dataset is determined based on the threshold value and a cumulative distribution of each of the one or more n-dimensional variables. The one or more first parameters are updated to generate one or more second parameters based on the estimated inverse cumulative distribution, wherein the updating is performed using an expectation-maximization algorithm. Finally, the model is created for each number in the range of numbers based on the one or more second parameters associated with each cluster in the number of clusters.

According to embodiments illustrated herein there is provided a method for stratifying one or more patients in one or more categories based on a medical record data associated with each of the one or more patients. The medical record data includes a measure of one or more physiological markers of each of the one or more patients. The method comprises receiving, by one or more processors, an input pertaining to a range of numbers. Each number corresponds to a number of categories in the medical record data. Each category corresponds to a medical condition associated with each of the one or more patients. For a category in the number of categories one or more first parameters of a distribution associated with the category are estimated. An inverse cumulative distribution of the one or more physiological markers is determined based on a threshold value and a cumulative distribution of each of the one or more physiological markers. The one or more first parameters are updated to generate one or more second parameters based on the estimated inverse cumulative distribution. The updating is performed using an expectation-maximization algorithm. A model is created for each number in the range of numbers based on the one or more second parameters associated with each category in the number of categories. A best model is selected from the model created for each number in the range of numbers using Bayesian information criteria. The best model is deterministic of the number of categories in the medical record data. The best model stratifies each of the one or more patients listed in the medical record data into the one or more categories.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not limit, the scope in any manner, wherein similar designations denote similar elements, and in which.

DETAILED DESCRIPTION

Figure 1:
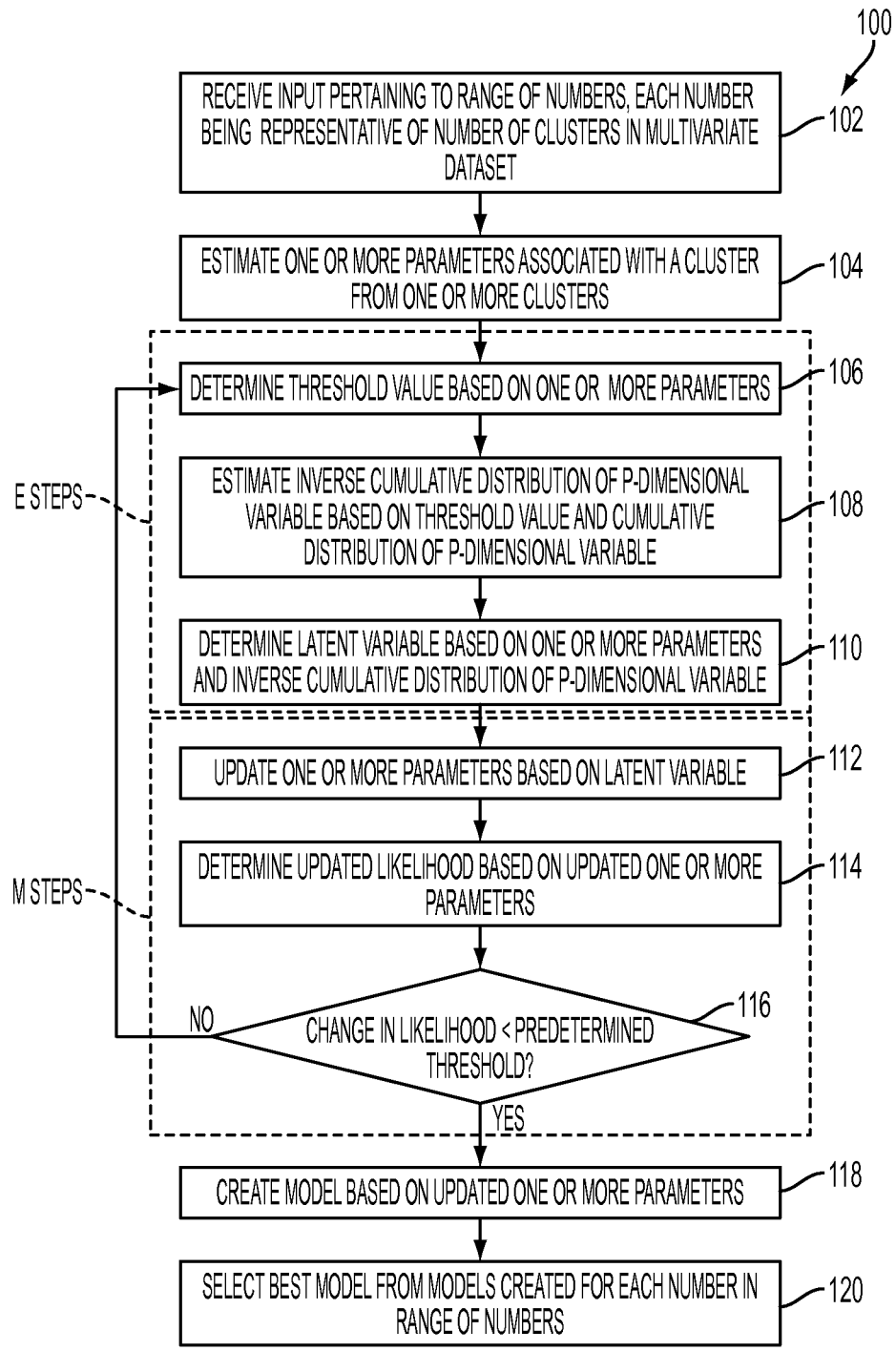
FIG. 1 is a flowchart illustrating a method for creating a model capable of identifying one or more clusters in a multivariate dataset.

The present disclosure is best understood with reference to the detailed figures and descriptions set forth herein. Various embodiments are discussed below with reference to the figures. However, those skilled in the art will readily appreciate that the detailed descriptions given herein with respect to the figures are simply for explanatory purposes, as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "at least one embodiment," "an embodiment," "one example", "an example", "for example" and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment.

Definitions: The following terms shall have, for the purposes of this application, the respective meanings set forth below.

"Multivariate dataset" refers to a dataset that includes observations of a p-dimensional variable. For example, 'n' realizations of p-dimensional variable may constitute a multivariate dataset. For example, a medical record data may include a measure of one or more physiological parameters of one or more patients. Such medical record data is an example of the multivariate dataset.

"Healthcare dataset" refers to a multivariate dataset that includes data obtained from the healthcare industry. In an embodiment, the healthcare dataset may correspond to a patient record data, hospital data, medical insurance data, diagnostics data, etc. In a scenario, where the healthcare data corresponds to the patient record data the one or more physiological parameters correspond to the p-dimensional variable and the number of records in the healthcare data corresponds to the realizations.

"Gaussian Mixture Model (GMM)" refers to a mathematical model that is capable of identifying one or more clusters in the multivariate dataset. In an embodiment, the data values in each of the one or more clusters are normally distributed (i.e., Gaussian distribution).

"Gaussian Copula Mixture Model (GCMM)" refers to a mathematical model that is capable of identifying one or more clusters in the multivariate dataset, where data values in each of the one or more clusters are distributed according to a Gaussian copula distribution.

A "cumulative distribution" refers to a distribution function, that describes the probability that a real-valued random variable X with a given probability distribution will be found at a value less than or equal to x.

An "inverse cumulative distribution" refers to an inverse function of the cumulative distribution of the random variable X.

A "mixing proportion of clusters" refer to a probability that a data value in the multivariate dataset belongs to different clusters. For example, the multivariate data includes two clusters. A probability that a data value in the multivariate data set belongs to the first cluster is 0.6. Then the probability that the data value will belong to the second cluster is 0.4. In an embodiment, the sum of probability of the data value in each of the one or more clusters in the dataset is one.

A "latent variable" refers to an intermediate variable that is not obtained from the multivariate dataset. In an embodiment, the latent variable is determined based on the one or more parameters.

"Probability" shall be broadly construed, to include any calculation of probability; approximation of probability, using any type of input data, regardless of precision or lack of precision; any number, either calculated or predetermined, that simulates a probability; or any method step having an effect of using or finding some data having some relation to a probability.

As discussed, the Gaussian mixture models are utilized for determining one or more clusters in a dataset. In order to determine the clusters, the Gaussian mixture models assume that data points in a cluster are normally distributed. In an embodiment, in most of the applications, the data points may not be normally distributed. Therefore, the Gaussian mixture models may not be able to predict the clusters in the dataset accurately.

In an embodiment, a Gaussian copula mixture model (GCMM) is another mathematical model that is utilized for identifying one or more clusters in a multivariate dataset. In an embodiment, the multivariate dataset may include data values of one or more p-dimensional variables. Each data value for each of the one or more p-dimensional variables may be a part of a cluster in the multivariate dataset. In an embodiment, the GCMM assumes that the data values in the cluster are derived from a Gaussian copula distribution. In an embodiment, copula corresponds to a multivariate probability distribution, for which marginal probability of each variable is uniformly distributed. In an embodiment, copulas are used for describing dependence between the one or more p-dimensional variables in the dataset. A typical Gaussian copula mixture model (GCMM) is represented by the following equation:

$$GCMM = \frac{\sum_{g=1}^{G} \pi_g \phi(y_i \mid \mu_g, \Sigma_g)}{\prod_{j=1}^{p} \psi_j(y_{i,j})} \quad (1)$$

where, $y_i$: Inverse cumulative distribution of p-dimensional random variable x;

p: Number of dimensions of random variable;

$\pi_g$: Mixing proportion of a cluster g with respect to other clusters in the multivariate dataset;

$\psi_j(y_{i,j})$: Marginal density of GMM along $j^{th}$ dimension;

G: Number of clusters in the multivariate dataset;

$\mu_g$: Mean of the Gaussian copula mixture component g;

$\Sigma_g$: Covariance matrix of p-dimensional variable x (representative of a covariance between the one or more clusters); and $\varphi(y_i \mid \mu_g, \Sigma_g)$: Multivariate Gaussian distribution of the data values in a cluster g with mean $\mu_g$ and variance as $\Sigma_g$.

In order to determine a number of clusters in the multivariate dataset and classify each data value of the one or more p-dimensional random variables, a GCMM is created. The creation of the GCMM, in an embodiment of the disclosure, has been described in conjunction with FIG. 1.

FIG. 1 is a flowchart 100 illustrating a method for creating a model capable of identifying one or more clusters in a multivariate dataset. In an embodiment, the model is a Gaussian copula mixture model (GCMM).

At step 102, an input is received from a user. In an embodiment, the input corresponds to a range of numbers. In an embodiment, the range of numbers corresponds to a number of GCM models that are to be created. Additionally, in an embodiment, each number in the range of numbers corresponds to a probable number of clusters that may be present in the multivariate dataset. For example, if the user inputs the range as 1 to 3, then, three GCM models will be created for each number in the range (i.e., 1, 2, and 3). Further, each number (i.e., 1, 2, and 3) is representative of the number of clusters in the multivariate dataset. For instance, for the number 3, in the range of numbers, the multivariate dataset may include three clusters. In an embodiment, the GCM models created for a particular number in the range of numbers will be able to identify that particular number of clusters in the multivariate dataset. For instance, the GCM model created for the number 3, in the range of numbers, will be able to identify three clusters in the multivariate dataset.

In addition, the multivariate dataset is received from the user. The multivariate dataset includes data values pertaining to a p-dimensional variable in the multivariate dataset. Hereinafter, the term data value has been interchangeably referred as realization. For the purpose of ongoing description, n realizations of the p-dimensional variable are present in the multivariate dataset.

At step 104, one or more parameters associated with a cluster from one or more clusters are estimated. Prior to determining the one or more parameters, a number is sequentially selected from the range of numbers. In an embodiment, the number corresponds to the number of clusters in the one or more clusters. For each cluster in the one or more clusters, the one or more parameters are determined. In an embodiment, the one or more parameters may include, but are not limited to, a mixing proportion of the one or more clusters, a mean of the distribution of the cluster (i.e., Gaussian copula mixture), a covariance between the one or more clusters. In an embodiment, the one or more parameters are estimated randomly. In an alternate embodiment, the one or more parameters are estimated using a k-means clustering algorithm. In an embodiment, the k-means clustering algorithm estimates the one or more parameters based on the following constraints:

$$\pi_g > 0 \quad (2)$$

$$\Sigma_{g=1}^{G} \pi_g = 1 \quad (3)$$

$$\Sigma_g \text{ is positive and definite} \quad (4)$$

$$\delta_i = \text{Min}_{g,j} |y_{i,j}^{(0)} - 2\kappa^{(0)}([\Sigma_g^{(0)} + I]^{-1} \Sigma_g^{(0)} I)_j| \quad (5)$$

where, $\pi_g$: Mixing proportions of the one or more clusters;

$\Sigma_g$: Covariance between the one or more clusters;

G: Number of clusters in the multivariate dataset;

$y_{i,j}^{(0)}$: Inverse cumulative distribution of the p-dimensional variable along the $j^{th}$ dimension; and $\kappa^{(0)}$: $\text{Max}(\mu_{g,j})$, where $\mu_{g,j}$ corresponds to mean of the distribution of the cluster g along the $j^{th}$ dimension.

A person having ordinary skill in the art would understand that the scope of the disclosure is not limited to estimating the one or more parameters using the k-means clustering algorithm. In an embodiment, any other technique such as decision tree and Gaussian mixture model may be used for estimating the one or more parameters.

At step 106, a threshold value is determined based on the one or more parameters. In an embodiment, the following equation is utilized to determine the threshold value:

$$\Gamma = \kappa^{(t)}([S^{(t)} + I]^{-1} S^{(t)} I)_j + \frac{1}{2}\left(1 + \frac{m^{(t)}}{p}\right)\delta_i \quad (6)$$

where,

Γ: Threshold value;

$$S^{(t)} = \Sigma_{g=1}^{G} Z_{ig}^{(t-1)} \Sigma_g^{(t)} \quad (7)$$

where $z_{ig}$ corresponds to a latent variable; and $m^{(t)}$: Sum of all elements of $S^{(t)}$.

In an embodiment, the latent variable corresponds to an intermediate variable that is not obtained from the multivariate dataset. In an embodiment, the latent variable is determined based on the one or more parameters. The determination of the latent variable, in an embodiment of the disclosure, has been described later.

At step 108, an inverse cumulative distribution of the p-dimensional variable is determined based on the threshold value (determined in the step 106) and the cumulative distribution of the p-dimensional variable. In an embodiment, the following equations are utilized to determine the inverse cumulative distribution:

$$y_{ij} = \left(\sum_{g=1}^{G} \frac{\pi_g^{(t)}}{\sigma_{g,jj}^{(t)}}\right)^{-1} \left[u_{ij} + \frac{1}{\sqrt{2\Pi}} \sum_{g=1}^{G} \frac{\pi_g^{(t)} \mu_{gj}^{(t)}}{\sigma_{g,jj}^{(t)}} - \frac{1}{2}\right] \quad (8)$$

$$y_{ij} = \text{Max}(y_{ij}, \Gamma) \quad (9)$$

where, $y_{ij}$: Inverse cumulative distribution of the p-dimensional variable along $j^{th}$ dimension; and $\sigma_{g,jj}^{(t)}$: $j^{th}$ diagonal element of the covariance matrix of the g-th cluster.

In an embodiment, the threshold value $\Gamma$ is a lower bound value for the inverse cumulative distribution of the p-dimensional variable. If at any instance, the determined value of the inverse cumulative distribution $y_{ij}$ is less than the threshold value $\Gamma$, the threshold value $\Gamma$ is selected as the value of the inverse cumulative distribution $y_{ij}$.

A person having ordinary skill in the art would understand that initially, when the one or more parameters are estimated using the k-means algorithm, the inverse cumulative distribution is determined based on the initial one or more parameters. In addition, based on the initial estimate of the inverse cumulative distribution, an initial likelihood is determined. In an embodiment, the initial likelihood corresponds to a probability that the initial one or more parameters are deterministic of the GCM model. In an embodiment, the initial likelihood is determined using the following equation:

$$\text{Inital likelihood} = \sum_{i=1}^{n} \log \sum_{g=1}^{G} \pi_g \frac{\sum_{g=1}^{G} \pi_g \phi(y_i \mid \mu_g, \Sigma_g)}{\prod_{j=1}^{p} \psi_j(y_{i,j})} \quad (10)$$

At step 110, the latent variable is determined based on the one or more parameters and the inverse cumulative distribution of the p-dimensional variable (determined in step 108). In an embodiment, the latent variable is determined using the following equation:

$$z_{ig}^{(t)} = \frac{\pi_g^{(t)} \phi(y_i^{(t)} \mid \mu_g^{(t)}, \Sigma_g^{(t)})}{\sum_{g=1}^{G} \pi_g^{(t)} \phi(y_i^{(t)} \mid \mu_g^{(t)}, \Sigma_g^{(t)})} \quad (11)$$

At step 112, the one or more parameters are updated based on the determined latent variable. In an embodiment, the one or more parameters are updated using following equations:

$$\pi_g^{(t+1)} = \frac{\sum_{i=1}^{n} z_{ig}^{(t)}}{n} \quad (12)$$

$$\mu_g^{(t+1)} = \frac{\sum_{i=1}^{n} z_{ig}^{(t)} y_i^{(t)}}{\sum_{i=1}^{n} z_{ig}^{(t)}} \quad (13)$$

$$\Sigma_g^{(t+1)} = \frac{\sum_{i=1}^{n} z_{ig}^{(t)} (y_i^{(t)} - \mu_g^{(t+1)})^T (y_i^{(t)} - \mu_g^{(t+1)})}{\sum_{i=1}^{n} z_{ig}^{(t)}} \quad (14)$$

At step 114, an updated likelihood is determined based on the updated one or more parameters. In an embodiment, the updated likelihood is determined using the following equation:

$$L^{(t+1)} = \prod_{i=1}^{n} \sum_{g=1}^{G} \pi_g^{(t+1)} \frac{1}{\sqrt{\det(2\pi \Sigma_g^{(t+1)})}} \quad (15)$$

$$\exp\left(-\frac{1}{2}(y_i^{(t)} - \mu_g^{(t+1)})^T \Sigma_g^{(t+1)-1}(y_i^{(t)} - \mu_g^{(t+1)})\right)$$

At step 116, a check is performed to determine whether a difference between the updated likelihood and the previous likelihood is less than a predefined threshold. In an embodiment, the previous likelihood corresponds to a likelihood that was determined in the previous iteration. For instance, during the first iteration of the method, the likelihood determined for the first iteration (t=1) is compared with the initial likelihood determined using equation 10. In a similar manner, in each iteration, the likelihood determined using the updated one or more parameters, for that iteration, is compared with the likelihood that was determined in the previous iteration. In an embodiment, the following equation is used to perform the check:

$$L^{(t+1)} - L^{(t)} < \in \quad (16)$$

where, $L^{(t+1)}$: Updated likelihood determined using the updated one or more parameters;

$L^{(t)}$: Likelihood determined in the previous iteration; and $\in$: Predefined threshold.

If at step 116 it is determined that the difference is greater than the predefined threshold, steps 106-116 are repeated. However, if at step 116 it is determined that the difference is less than the predefined threshold, the updated one or more parameters are considered as the parameters of the model.

At step 118, a model is created based on the updated one or more parameters. In an embodiment, the following equation represents the model:

$$\text{GCM model} = \Pi_{i=1}^{n} \Sigma_{g=1}^{G} \pi_g \Pi_{i=1}^{n} [C((u_{i1}, \ldots, u_{ip}) \mid v) \\ \Pi_{j=1}^{p} f_j(x_{ij})] \quad (17)$$

where, $u_{ip}$: Cumulative distribution of the p-dimensional variable;

C: Copula function (represented by equation 1) of the p-dimensional variable;

$f_j(x_{ij})$: Joint distribution of the p-dimensional variable; and v: Vector of the one or more parameters.

In an embodiment, the steps 104-118 are repeated for each number in the range of numbers, to create the model for each number in the range of numbers. Thus, the number of models that will be created is equal to the range of numbers.

At step 120, a best model is selected from the model created for each number in the range of numbers. In an embodiment, the best model is selected using Bayesian Information Criterion (BIC). In order to determine the best model, a score is determined for each model created for the numbers in the range of numbers. In an embodiment, the following equation is used for determining the score:

$$\text{BIC score} = 2 \log \mathcal{L}(\hat{v}|(u_{i1}, \ldots, u_{ip}) - \rho \log n \qquad (18)$$

where, $\hat{v}$: The one or more updated parameters that are used for creating the model in step 118;

$\mathcal{L}$: The likelihood estimated (using equation 15) for the one or more updated parameters, which are used for creating the model in step 118;

ρ: Number of free parameters; and n: Number of data values or realizations.

In an embodiment, the free parameters correspond to parameters that do not depend on the one or more parameters or the multivariate dataset. The free parameters are determined independently. In an embodiment, the number of free parameters for p-dimensional data and G clusters is determined using the following equation:

$$\rho = (G-1) + Gp + Gp(p+1)/2 \qquad (19)$$

In an embodiment, the model that has the best BIC score is selected as the best model. Further, in an embodiment, the number (from the range of numbers), for which the best model is created, corresponds to the number of clusters present in the multivariate dataset. For example, if the range of numbers is 1-3, three models will be created, one for each number, i.e., 1, 2, and 3. Further, if the model created for the number 2 has the maximum BIC score, the second model, which corresponds to the number 2, is selected. Additionally, in this case, the number of clusters that will be present in the multivariate dataset is two.

A person having ordinary skill in the art would understand that the number of clusters determined in step 120 is an estimate of the number of clusters present in the multivariate dataset. In an embodiment, the multivariate dataset may include more than the estimated number of clusters.

In an embodiment, the models created for each number in the range of numbers are mixture models. In an embodiment, the mixture model corresponds to a probabilistic model that has the capability of identifying one or more clusters in the multivariate dataset. Post selection of the best model, the best model is used to categorize each data point (realization of the p-dimensional variable) in the multivariate dataset into the one or more clusters.

In an embodiment, the method described in the flowchart 100 corresponds to an Expectation-Maximization (EM) algorithm. Each iteration of the EM algorithm alternates between performing a set of expectation (E) steps, which create a function for the expectation of the log-likelihood evaluated using the current estimate for the parameters (determination of the latent variable), and a set of maximization (M) steps, which compute the parameters maximizing the expected log-likelihood found in the E steps. In an embodiment, steps 106, 108, and 110 correspond to the E steps of the EM algorithm, while steps 112, 114, and 116 correspond to the M steps of the EM algorithm.

Figure 2:
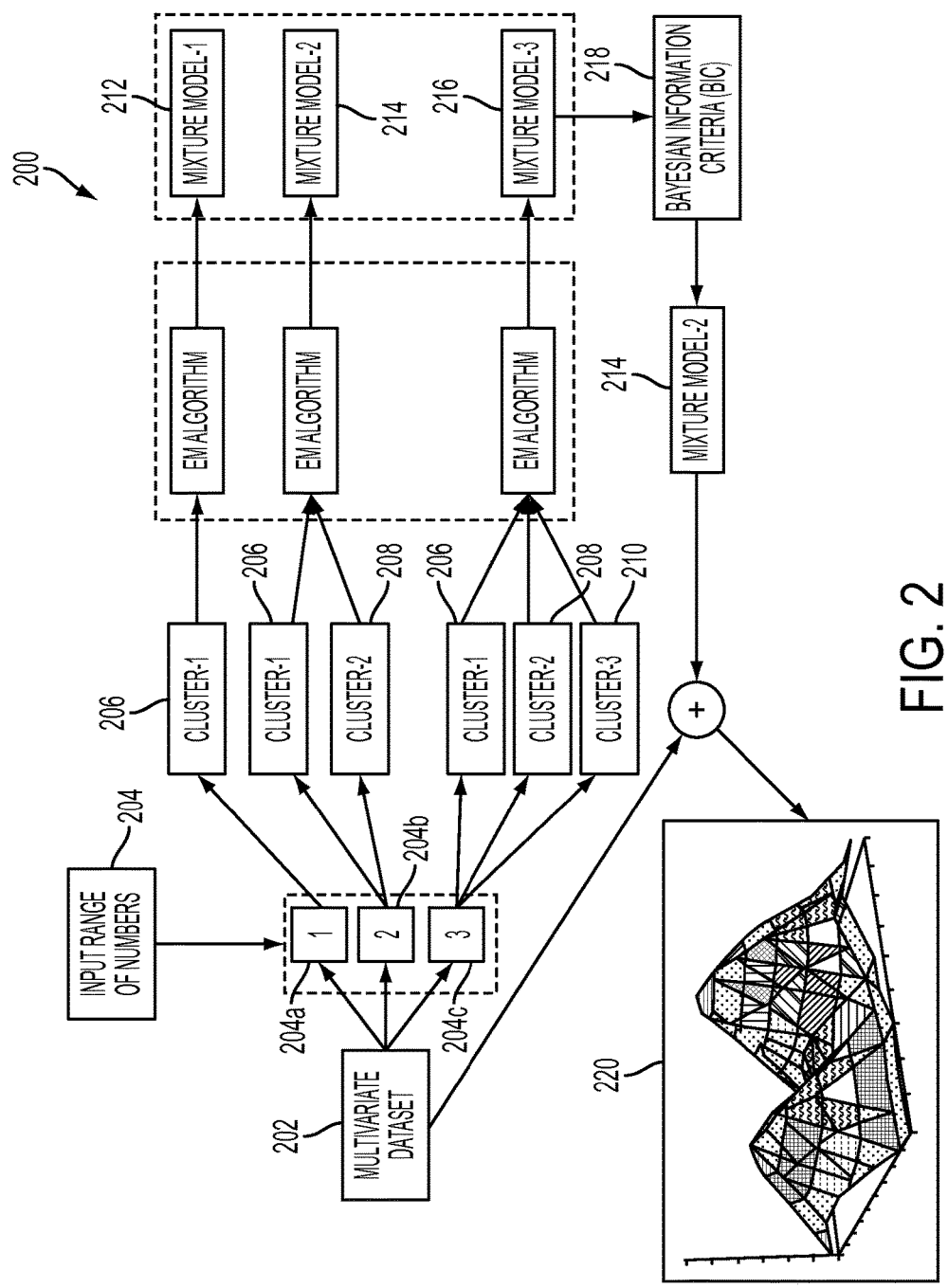
FIG. 2 is a flow diagram illustrating creation of the model, in accordance with at least one embodiment.

FIG. 2 is a flow diagram 200 illustrating creation of the model, in accordance with at least one embodiment. The flow diagram 200 has been described in conjunction with FIG. 1.

The multivariate dataset (depicted by 202) is received from the user. In addition, the range of numbers (depicted by 204) is received from the user. For instance, the range of number include (1 (depicted by 204a), 2 (depicted by 204b), and 3 (depicted by 204c)). As discussed above, each number corresponds to a probable number of clusters present in the multivariate dataset 202. For instance, for the number 1 (depicted by 204a), it is assumed that the multivariate dataset 202 includes only one cluster (i.e., cluster-1 (depicted by 206)). Similarly, for the number 2 (depicted by 204b), it is assumed that the multivariate dataset 202 includes two clusters (i.e., cluster-1 (depicted by 206) and cluster-2 (depicted by 208)). Further, for the number 3 (depicted by 204c), in the range of numbers (depicted by 204), it is assumed that the multivariate dataset 202 includes a third cluster (cluster-3 (depicted by 210)) in addition to the two clusters 206 and 208. For each number in the range of numbers, the EM algorithm is executed. In an embodiment, the EM algorithm estimates the one or more parameters of a mixture model capable of clustering the data points into the one or more clusters, where the number of clusters is determined based on the number in the range of numbers. For example, the EM algorithm executed for the cluster-1 (depicted by 206) will generate the mixture model-1 212 that will be able to cluster the data values in the multivariate dataset 202 in the cluster-1 (depicted by 206). Similarly, the mixture model-2 (depicted by 214) is generated for the number 2 (depicted by 204b). The mixture model-2 (depicted by 214) will be able to cluster the data values in the two clusters (i.e., cluster-1 (depicted by 206) and cluster-2 (depicted by 208)).

Post creation of the mixture models for each number in the range of numbers, a BIC score is determined for each mixture model using equation 18 (depicted by 218). For instance, if the mixture model-2 (depicted by 214) has the maximum BIC score, the mixture model-2 (depicted by 214) is selected. Further, as the mixture model-2 (depicted by 214) has been obtained for the number 2 (depicted by 204b) in the range of numbers (depicted by 204), the number of probable clusters in the multivariate dataset 202 are two. Post selection of the mixture model-2 (depicted by 214), the mixture model-2 (depicted by 214) is used for clustering (depicted by 220) the multivariate dataset 202.

Figure 3:
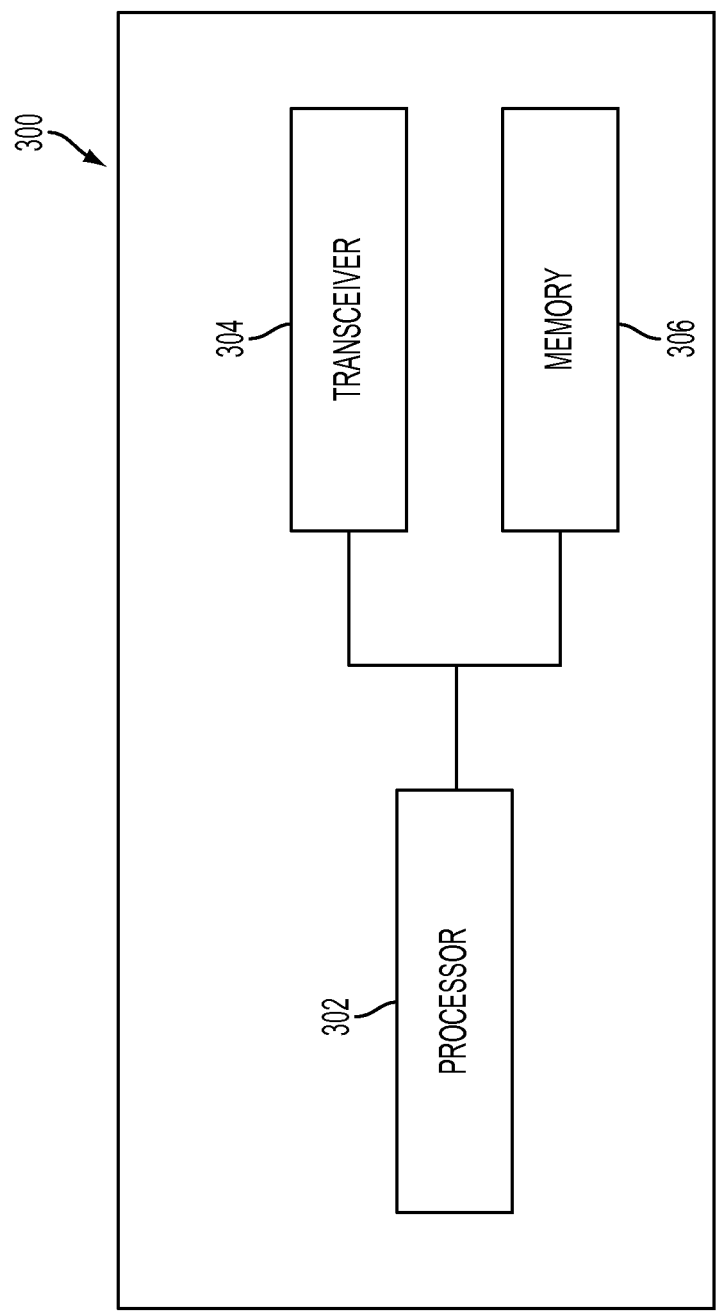
FIG. 3 is a block diagram of a computing device that is capable of creating the model, in accordance with at least one embodiment.

FIG. 3 is a block diagram of a computing device 300 that is capable of creating the model, in accordance with at least one embodiment. The computing device 300 includes a processor 302, a transceiver 304, and a memory 306. The processor 302 is coupled to the transceiver 304 and the memory 306.

The processor 302 includes suitable logic, circuitry, and interfaces and is configured to execute one or more instructions stored in the memory 306 to perform predetermined operations on the computing device 300. The memory 306 may be configured to store the one or more instructions. The processor 302 may be implemented using one or more processor technologies known in the art. Examples of the processor 302 include, but are not limited to, an X86 processor, a RISC processor, an ASIC processor, a CISC processor, or any other processor.

The transceiver 304 transmits and receives messages and data. Further, the transceiver is capable of receiving the multivariate dataset and the range of numbers from the user. Examples of the transceiver 304 may include, but are not limited to, an antenna, an Ethernet port, a universal serial bus (USB) port, or any other port that can be configured to receive and transmit data. The transceiver 304 transmits and receives data and messages in accordance with various communication protocols, such as, TCP/IP, UDP, and 2G, 3G, or 4G communication protocols.

The memory 306 stores a set of instructions and data. Some of the commonly known memory implementations include, but are not limited to, a RAM, a read-only memory (ROM), a hard disk drive (HDD), and a secure digital (SD) card. Further, the memory 306 includes the one or more instructions that are executable by the processor 302 to perform specific operations. It is apparent to a person having ordinary skill in the art that the one or more instructions stored in the memory 306 enable the hardware of the computing device 300 to perform the predetermined operations. In an embodiment, the computing device 300 is configured to execute the flowchart 100 to generate the model that is capable of identifying the one or more clusters in the multivariate dataset.

In an embodiment, the method described in the flowchart 100 may be applicable in analyzing data from the health care sector. For instance, the patients can be stratified by discovering patterns in disease risk profiles and treatment responses. The method can be further applied at different levels in the health care industry such as at individual patient levels by analysis of Electronic Medical Records (EMR), or at hospital level (for example, identifying a group of patients having risk of getting involved in health insurance frauds).

Figure 4:
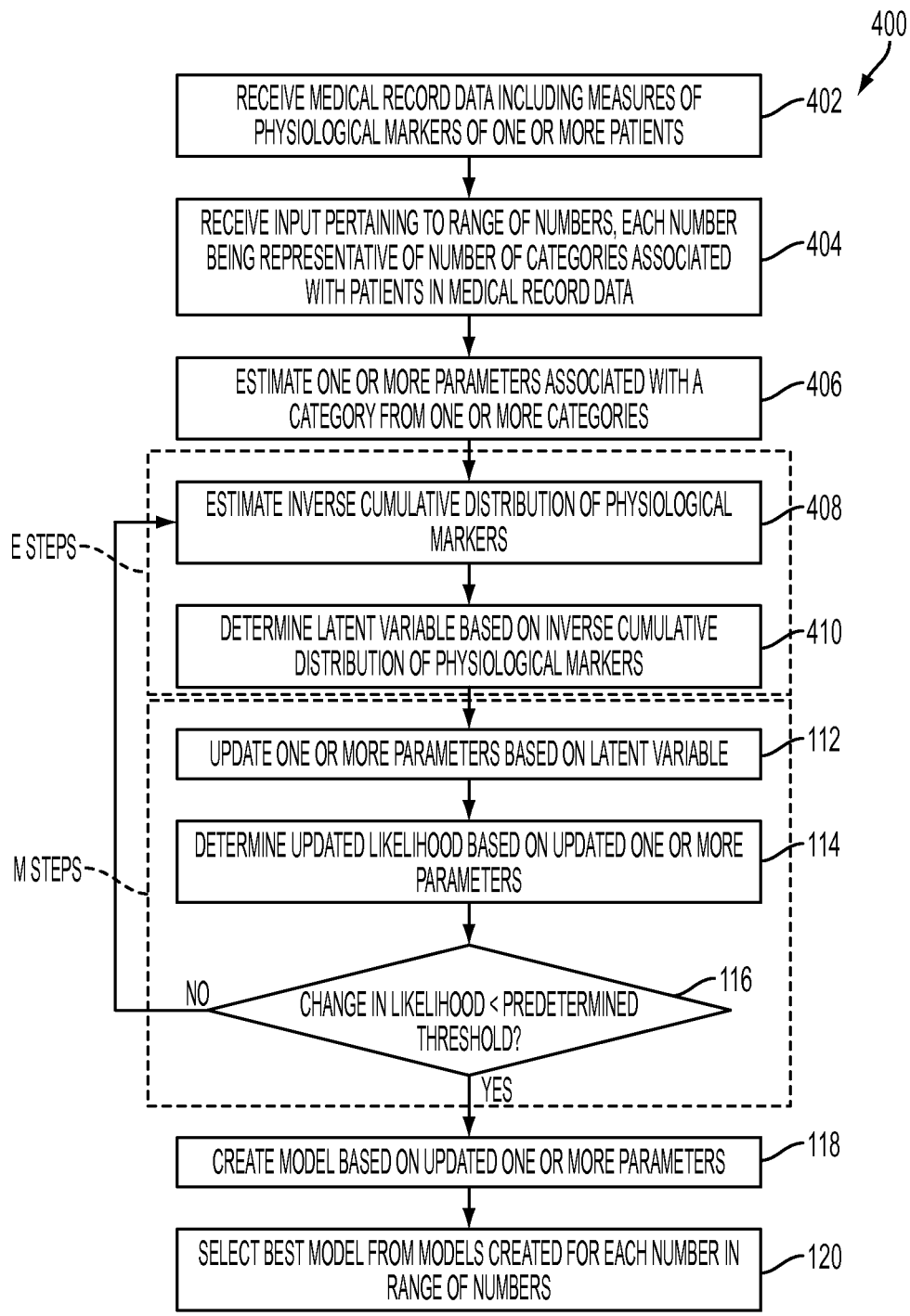
FIG. 4 is flowchart illustrating a method to stratify one or more patients based on medical record data associated with the one or more patients, in accordance with at least one embodiment.

FIG. 4 is flowchart 400 illustrating a method for stratifying one or more patients based on medical record data associated with the one or more patients, in accordance with at least one embodiment.

At step 402, medical record data is received from the user. In an embodiment, the processor 302 receives the medical record data. In an embodiment, the medical record data includes various measures of various physiological markers of one or more patients such as, but not limited to, age, blood pressure, serum cholesterol, heart rate, and ST depression. In an embodiment, the physiological marker corresponds to the p-dimensional variable with age, blood pressure, serum cholesterol, heart rate, and ST depression as the different dimensions.

A person having ordinary skill in the art would understand that the scope of disclosure is not limited to the aforementioned physiological markers. In an embodiment, various other physiological markers can be used.

At step 404, an input is received from the user pertaining to a range of numbers. In an embodiment, the processor 302 receives the input through the transceiver 304. In an embodiment, the range of number corresponds to a probable number of categories associated with the patients that may be present in the medical record data. In an embodiment, the categories in the medical record data may correspond to a health condition of the one or more patients. For instance, the one or more patients may be stratified under two categories as having a heart disease or not having a heart disease.

At step 406, one or more parameters associated with a category from the one or more categories are estimated. In an embodiment, the processor 302 estimates the one or more parameters in a similar manner as described in the step 104.

At step 408, an inverse cumulative distribution of the physiological markers is estimated. In an embodiment, the processor 302 estimates the inverse cumulative distribution. Prior to estimating the inverse cumulative distribution, the processor 302 determines the threshold value, which is a lower bound for the inverse cumulative distribution of the physiological markers. In an embodiment, the threshold value and the inverse cumulative distribution may be determined as described in the steps 106 and 108, respectively.

Based on the inverse cumulative distribution of the physiological parameters, an initial likelihood is determined by using the equation 10.

At step 410, a latent variable is determined based on the inverse cumulative distribution of the physiological markers. In an embodiment, the processor 302 determines the latent variable. In an embodiment, the processor 302 performs the step 110 to determine the latent variable.

At step 112, the one or more parameters are updated based on the latent variable. In an embodiment, the processor 302 is configured to update the one or more parameters. At step 114, an updated likelihood is determined based on the updated one or more parameters. In an embodiment, the processor 302 determines the updated likelihood. At step 116, a check is performed to determine whether a difference between the updated likelihood and the previous likelihood is less than a predefined threshold. If at step 116 it is determined that the difference is greater than the predefined threshold, 408-116 are repeated. However, if at step 116 it is determined that the difference is less than the predefined threshold, the updated one or more parameters are considered as the parameters of the model. Further, at step 118, a model is created based on the updated one or more parameters.

In an embodiment, the aforementioned steps are repeated for each number in the range of numbers. In an embodiment, the number of models created is equal to the total numbers present in the range of numbers. Further, at step 120, a best model is selected from the models created for the numbers in the range of numbers. In an embodiment, the number, from the range numbers, for which the best model is selected, represents the number of categories present in the medical record data. For instance, if the best model is created for the number 2, the best model will be able to categorize the medical record data into two categories (e.g., patients with a heart disease and patients without a heart disease).

Post creation of the models and the selection of the best model, the selected model are used to stratify the one or more patients in two categories, i.e., patients having a heart disease and patients not having any heart disease. In an embodiment, the best model categorizes the medical record data in the two categories based on the physiological parameters listed in the medical record data.

A person having ordinary skill in the art would understand that in a scenario where new data is inputted by the user, the trained model can categorize the data in the corresponding clusters based on the value of the p-dimensional variable. For instance, when physiological parameters of new patients are inputted to the system, the model will categorize the new patients in one of the two categories (i.e., having a heart disease, or not having the heart disease).

A person having ordinary skill in the art would understand that the scope of the disclosure should not be limited to stratifying the one or more patients in the one or more categories. In an embodiment, similar medical data can be analyzed to draw out different inferences. For instance, insurance data pertaining to health care may be analyzed to determine health insurance frauds.

For example, if the healthcare data correspond to the medical insurance data, the p-dimensional variable in the medical insurance data may corresponds one or more insurance related parameters such as age of the insured person, one or more physiological parameters of the insured person, premium being paid by the insured person, insurance amount, and coverage limit. The process described in the flowchart 100 and 400 can be utilized to determine insurance frauds, recommend insurance amounts, etc. Similarly, the hospital data may be analyzed to help doctors to make decisions or diagnosis.

The disclosed embodiments encompass numerous advantages. The estimation of the inverse cumulative distribution of the p-dimensional variable enables the usage of the expectation maximization algorithm to generate the GCMM. Further, the number of clusters present in the multivariate dataset is also estimated. This enables the system to be more dynamic and provides adaptability. Suppose, the system receives an unknown multivariate dataset. The user may enter a range of numbers that he/she feels should be the number of clusters in the multivariate dataset. The system creates a model for each number and from the models so created a best model is selected. The number from the range of number that corresponds to the selected best model is representative of the number of clusters present in the multivariate dataset. This capability of estimating the number of clusters makes the system adaptive. Further, this adaptive system can be used to identify clusters in any multivariate dataset such as healthcare related data.

The disclosed methods and systems, as illustrated in the ongoing description or any of its components, may be embodied in the form of a computer system. Typical examples of a computer system include a general purpose computer, a programmed microprocessor, a micro-controller, a peripheral integrated circuit element, and other devices or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, 'C', 'C++', 'Visual C++' and 'Visual Basic'. Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, 'Unix', DOS', 'Android', 'Symbian', and 'Linux'.

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of methods and systems for analyzing healthcare data have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A method for determining a diagnosis procedure by a computing device, the method comprising:
receiving a healthcare data set, wherein the healthcare data set comprises a plurality of healthcare records for a plurality of patients, wherein the healthcare data set corresponds to at least one of a medical record data, or hospital data, or medical insurance data, and wherein each healthcare record in the plurality of healthcare records comprises one or more physiological markers for a patient in the plurality of patients;
receiving, by one or more processors at the computing device, an input pertaining to a range of numbers, wherein the range of numbers represents a probable number of categories of health conditions for the plurality of patients;
for each number in the range of numbers:
estimating, by the one or more processors, one or more first parameters of a distribution associated with a category from the categories of health conditions;
estimating, by the one or more processors, an inverse cumulative distribution of each of one or more n-dimensional variables in the healthcare dataset based on a threshold value and a cumulative distribution of each of the one or more n-dimensional variables, wherein the one or more n-dimensional variables comprise the one or more physiological markers in the healthcare dataset;
determining one or more latent variables based on the inverse cumulative distribution of each of the one or more n-dimensional variables, wherein the one or more latent variables comprise conditions in the plurality of patients not directly represented in the physiological markers;
updating, by the one or more processors, the one or more first parameters to generate one or more second parameters based on the one or more latent variables, wherein the updating is performed using an expectation-maximization algorithm;
creating, by the one or more processors, a model for each number in the range of numbers based on the one or more second parameters associated with the category from the categories of health conditions; and
determining, by the one or more processors, a score for each model, created for each number in the range of numbers, based on the one or more second parameters, an estimated likelihood value for the one or more second parameters, a first count of one or more free parameters, and a second count of data values corresponding to the one or more n-dimensional variables;
selecting, by the one or more processors, a best model from models created for the range of numbers based on scores corresponding to the models;
applying the healthcare data set to the best model, wherein the best model categorizes the plurality of patents in one or more of the categories of health conditions based on the one or more physiological markers in the healthcare dataset; and
determining, by the one or more processors, a diagnosis of at least one patient from the plurality of patients based on the categorization of the plurality of patients in the categories of health conditions for providing assistance to a medical practitioner.

2. The method of claim 1, wherein the one or more physiological markers comprise at least one of a blood glucose level, a blood pressure, an age, a serum cholesterol, or a maximum heart rate.

3. The method of claim 1, wherein the medical insurance data includes one or more insurance related parameters.

4. The method of claim 3, wherein the one or more insurance related parameters correspond to the n-dimensional variable.

5. The method of claim 3, wherein the one or more insurance related parameters comprise at least one of age of the insured person, one or more physiological parameters of the insured person, premium being paid by the insured person, insurance amount, and coverage limit.

6. The method of claim 1, wherein the one or more first parameters of the distribution associated with the category comprise a measure of mixing proportions of one or more clusters in the dataset, number of clusters, a mean of the distribution, and a covariance between the one or more clusters.

7. The method of claim 1, wherein the cumulative distribution of each of the one or more n-dimensional variables is determined from the healthcare dataset.

8. The method of claim 1, wherein the distribution associated with the category corresponds to a Gaussian copula distribution.

9. The method of claim 1, wherein the expectation-maximization algorithm further comprises determining, by the one or more processors, a first likelihood of the one or more first parameters being deterministic of the model.

10. The method of claim 9, wherein the expectation-maximization algorithm further comprises determining, by the one or more processors, a second likelihood of the one or more second parameters being deterministic of the model.

11. The method of claim 10 further comprising comparing, by the one or more processors, the first likelihood and the second likelihood.

12. The method of claim 11, wherein the model is created using the one or more second parameters based on the comparison.

13. The method of claim 11, wherein the threshold value, and the inverse cumulative distribution are updated using the one or more second parameters based on the comparison.

14. The method of claim 13, wherein the one or more second parameters are updated using the updated threshold value and the updated inverse cumulative distribution based on the comparison, wherein the second likelihood is updated based on the updated one or more second parameters.

15. The method of claim 1, wherein the selection of the best model from the models created for each number in the range of numbers is performed by using Bayesian information criteria, wherein the best model is deterministic of the number of categories in the healthcare dataset.

16. The method of claim 1, wherein the one or more first parameters are estimated based on at least one of a k-means algorithm.

17. The method of claim 1 further comprising determining, by the one or more processors, the threshold value based on the one or more first parameters.

18. A system for determining a diagnosis procedure the system comprising:
one or more processors at a computing device configured to:

receive a healthcare dataset, wherein the healthcare data set comprises a plurality of healthcare records for a plurality of patients, wherein the healthcare data set corresponds to at least one of a medical record data, or hospital data, or medical insurance data, and wherein each healthcare record in the plurality of healthcare records comprises one or more physiological markers for a patient in the plurality of patients;

receive, by one or more processors, an input pertaining to a range of numbers wherein represents a probable number of categories of health conditions for the plurality of patients;

for each number in the range of numbers:
  estimate one or more first parameters of a distribution associated with a category from the categories of health conditions;
  determine a threshold value based on the one or more first parameters;
  estimate an inverse cumulative distribution of each of one or more n-dimensional variables in the healthcare dataset based on the threshold value and a cumulative distribution of each of the one or more n-dimensional variables, wherein the one or more n-dimensional variables comprise the one or more physiological markers in the healthcare dataset;
  determine one or more latent variables based on the inverse cumulative distribution of each of the one or more n-dimensional variables, wherein the one or more latent variables comprise conditions in the plurality of patients not directly represented in the physiological markers;
  update the one or more first parameters to generate one or more second parameters based on the one or more latent variables, wherein the updating is performed using an expectation-maximization algorithm;
  create a model for each number in the range of numbers based on the one or more second parameters associated with the category from the categories of health conditions; and
  determine a score for each model, created for each number in the range of numbers, based on the one or more second parameters, an estimated likelihood value for the one or more second parameters, a first count of one or more free parameters, and a second count of data values corresponding to the one or more n-dimensional variables;

select a best model from the models created for the range of numbers based on scores corresponding to the models;

apply the healthcare data set to the best model, wherein the best model categorizes the plurality of patents in one or more of the categories of health conditions based on the one or more physiological markers in the healthcare dataset; and determine a diagnosis of at least one patient from the plurality of patients based on the categorization of the plurality of patients in the categories of health conditions for providing assistance to a medical practitioner.

19. The system of claim 18, wherein the cumulative distribution of each of the one or more n-dimensional variables is determined from the healthcare dataset.

20. The system of claim 18, wherein the distribution associated with the category corresponds to a Gaussian copula distribution.

21. The system of claim 18, wherein the expectation-maximization algorithm further comprises determining a first likelihood of the one or more first parameters being deterministic of the model.

22. The system of claim 21, wherein the expectation-maximization algorithm further comprises determining a second likelihood of the one or more second parameters being deterministic of the model.

23. The system of claim 22, wherein the one or more processors are further configured to compare the first likelihood and the second likelihood.

24. The system of claim 23, wherein the model is created using the one or more second parameters based on the comparison.

25. The system of claim 23, wherein the threshold value, and the inverse cumulative distribution are updated using the one or more second parameters based on the comparison.

26. The system of claim 25, wherein the one or more second parameters are updated using the updated threshold value and the updated inverse cumulative distribution based on the comparison, wherein the second likelihood is updated based on the updated one or more second parameters.

27. The system of claim 18, wherein the selection of the best model from the models created for each number in the range of numbers is performed by using Bayesian information criteria, wherein the best model is deterministic of the number of categories in the healthcare dataset.

28. A computer program product for use with a computing device, the computer program product comprising a non-transitory computer readable medium, the non-transitory computer readable medium stores a computer program code for determining a diagnosis procedure, the computer program code is executable by one or more processors in the computing device to:

receive a healthcare dataset, wherein the healthcare data set comprises a plurality of healthcare records for a plurality of patients, wherein the healthcare data set corresponds to at least one of a medical record data, or hospital data, or medical insurance data, and wherein each healthcare record in the plurality of healthcare records comprises one or more physiological markers for a patient in the plurality of patients;

receive an input pertaining to a range of numbers, wherein the range of numbers represents a probable number of categories of health conditions for the plurality of patients;

for each number in the range of numbers:
  estimate one or more first parameters of a distribution associated with a category from the categories of health conditions;
  determine a threshold value based on the one or more first parameters;
  estimate an inverse cumulative distribution of each of one or more n-dimensional variables in the healthcare dataset based on the threshold value and a cumulative distribution of each of the one or more n-dimensional variables, wherein the one or more n-dimensional variables comprise the one or more physiological markers in the healthcare dataset;
  determine one or more latent variables based on the inverse cumulative distribution of each of the one or more n-dimensional variables, wherein the one or more latent variables comprise conditions in the plurality of patients not directly represented in the physiological markers;
  update the one or more first parameters to generate one or more second parameters based on the one or more latent variables, wherein the updating is performed using an expectation-maximization algorithm;

create a model for each number in the range of numbers based on the one or more second parameters associated with the category from the categories of health conditions; and determine a score for each model, created for each number in the range of numbers, based on the one or more second parameters, an estimated likelihood value for the one or more second parameters, a first count of one or more free parameters, and a second count of data values corresponding to the one or more n-dimensional variables;

select a best model from the models created for the range of numbers based on scores corresponding to the models;

apply the healthcare data set to the best model, wherein the best model categorizes the plurality of patents in one or more of the categories of health conditions based on the one or more physiological markers in the healthcare dataset; and determine a diagnosis of at least one patient from the plurality of patients based on the categorization of the plurality of patients in the categories of health conditions for providing assistance to a medical practitioner.

* * * * *